(12) United States Patent
Hurwitz

(10) Patent No.: US 6,991,842 B2
(45) Date of Patent: *Jan. 31, 2006

(54) SCENT DISPERSING MAT APPARATUS

(76) Inventor: Marni Hurwitz, 81 Mosle Rd., Far Hills, NJ (US) 07931

( * ) Notice: Subject to any disclaimer, the term of this patent is extended or adjusted under 35 U.S.C. 154(b) by 42 days.

This patent is subject to a terminal disclaimer.

(21) Appl. No.: 10/712,343

(22) Filed: Nov. 14, 2003

(65) Prior Publication Data

US 2004/0121111 A1    Jun. 24, 2004

Related U.S. Application Data

(60) Provisional application No. 60/426,038, filed on Nov. 14, 2002.

(51) Int. Cl.
*B32B 3/10*   (2006.01)

(52) U.S. Cl. .................. 428/71; 428/68; 428/138; 428/905; 239/56; 239/55; 15/215; 15/217

(58) Field of Classification Search .................. 428/68, 428/71, 138, 905; 239/55, 56, 34, 309, 326; 15/215, 216, 217; 52/177, 181
See application file for complete search history.

(56) References Cited

U.S. PATENT DOCUMENTS 4,161,284 A * 7/1979 Rattan ..................... 239/43
6,254,836 B1 * 7/2001 Fry ......................... 422/124

* cited by examiner

*Primary Examiner*—Alexander S. Thomas
(74) *Attorney, Agent, or Firm*—Ernest D. Buff & Associates, LLC; Ernest D. Buff; Theodore J. Pierson

(57) ABSTRACT

A scent dispersing apparatus, such as a mat, capable of enclosing a scent-containing element inside an air-filled cavity. A housing contains a means for air ventilation, such as small air holes, for dispersion of scent. When the housing receives a force, such as a user exerting pressure upon on the housing, air is pushed from the air cavity outward through the air holes, thereby, dispersing scent contained in the scented insert. Additional air enters the air cavity once the pressure is released through an elastic rebound effect.

8 Claims, 7 Drawing Sheets

SCENT DISPERSING MAT APPARATUS

This application claims the benefit of provisional application No. 60/426,038 filed Sep. 14, 2002.

FIELD OF THE INVENTION

The present invention relates to an apparatus for dispersing scent, and in particular, an apparatus capable of housing a scented insert for dispersion of scent when the apparatus receives a force or is compressed.

SUMMARY

In an illustrative, non-limiting implementation, a scent dispersing apparatus is provided. The scent dispersing apparatus comprises a housing, such as a floor mat, capable of enclosing a scented insert inside an air-filled cavity. The housing contains a means for air ventilation, such as small air holes, for dispersion of scent. When the housing receives a force; such as a user stepping on the housing, air is pushed from the air cavity outward through the air holes, thereby, dispersing scent contained in the scented insert.

DESCRIPTION OF THE PREFERRED EMBODIMENTS

Figure 1A:
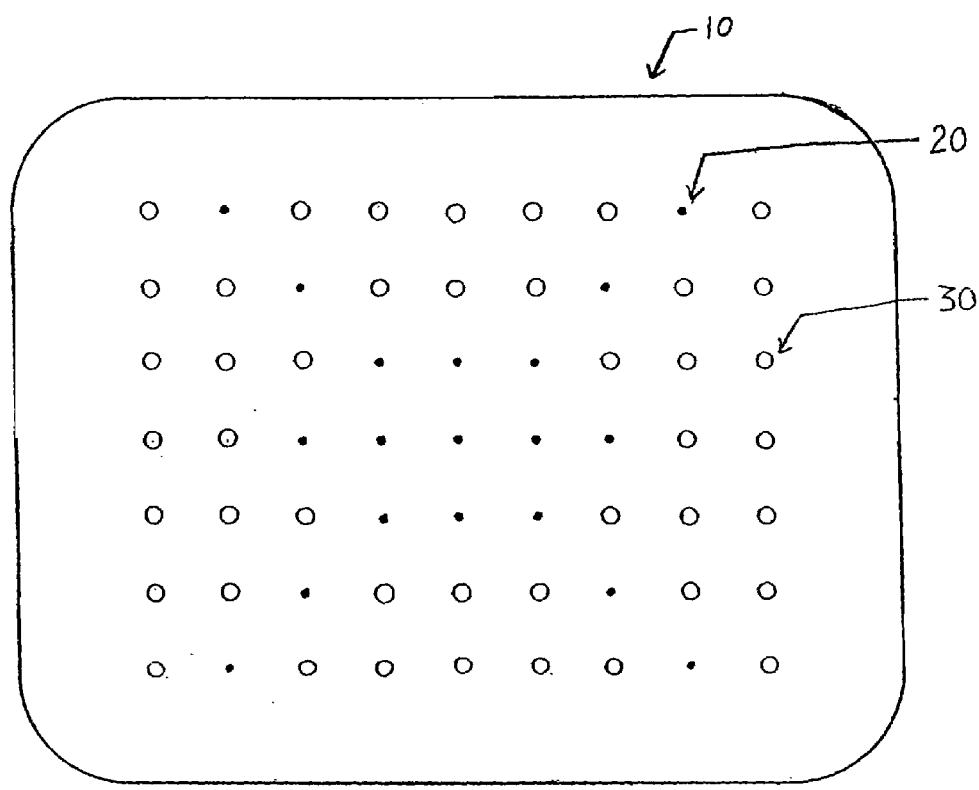
FIG. 1A is a plan view of an example of a scent dispensing/dispersing apparatus according to the present invention.
Figure 1B:
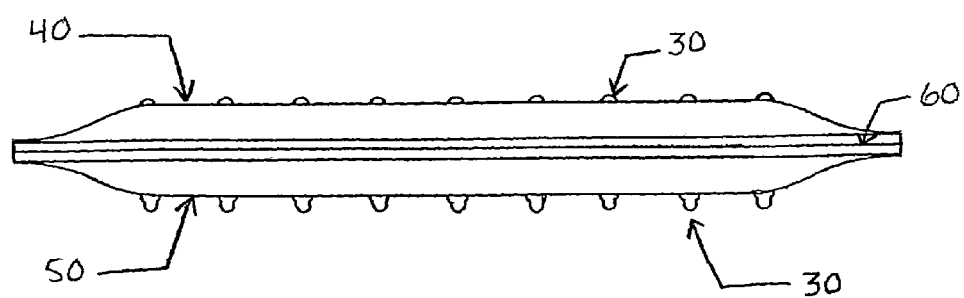
FIG. 1B is a side view thereof.

FIGS. 1A and 1B show a scent dispersing apparatus in accordance with an illustrative non-limiting embodiment of the present invention. As shown in FIG. 1A, the apparatus is a mat 10 having air holes 20 and protrusions 30. In FIG. 1B, the mat 10 is shown to have a top portion 40 and a bottom portion 50, which are sealed together at seal 60. Protrusions 30 are shown on both the top portion 40 and bottom portion 50 of mat 10, but may be limited to the bottom portion 50 or disposed with entirely, as necessary in the particular application.

Figure 2:
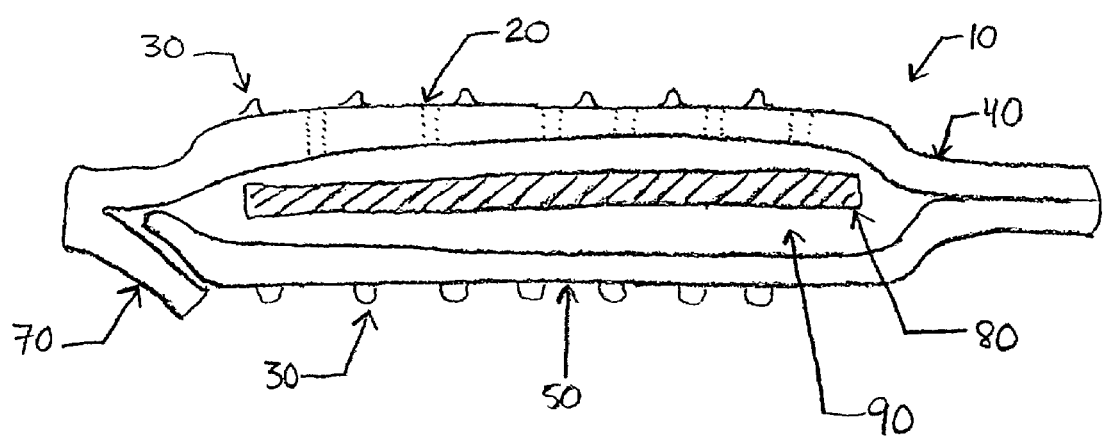
FIG. 2 illustrates a second embodiment thereof in side view.

A cross sectional view of mat 10 is shown in FIG. 2. As shown, a scented insert 80 is placed in an air cavity 90, formed between top portion 40 and lower portion 50. The non-limiting embodiment of FIG. 2 further shows flap 70 for entry and removal of insert 80 and for closing mat 10. Air holes 20 allow scent from insert 80 to disperse from air cavity 90 when mat 10 is stepped on or receives some other force by a user.

The top portion 40 and bottom portion 50 of mat 10 can be made of a synthetic material, such as, rubber, plastic or other resilient material capable of deformation. Mat 10 may also be made of a thin deformable metal material for more industrial type uses or areas receiving heavy traffic. Mat 10 may be any size or texture for a variety of uses, such as a car, kitchen, bathroom or door mat. Although mat 10 is shown in FIG. 1A as rectangular in shape, the shape may vary according to a user's preference.

Figure 5:
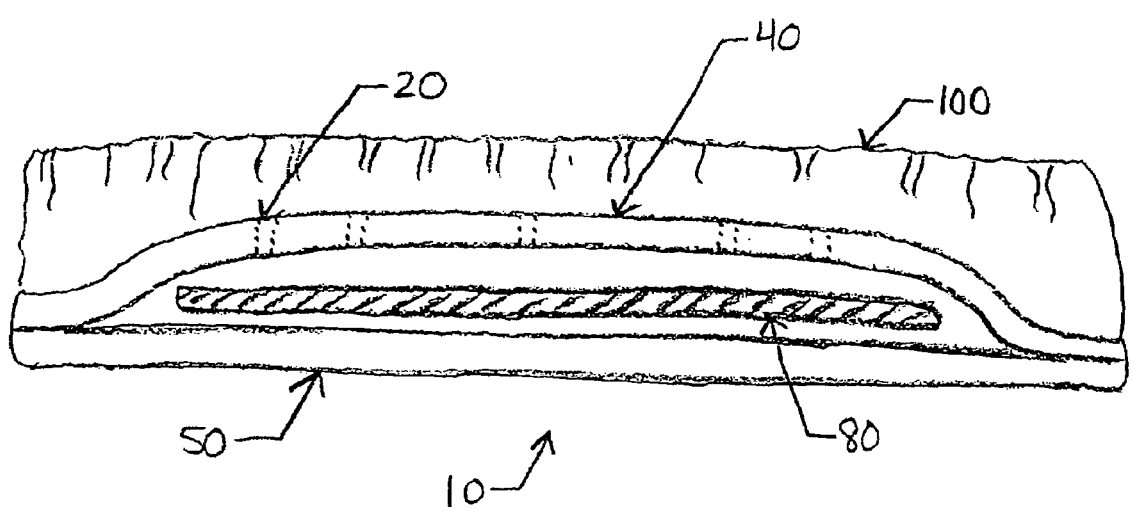
FIG. 5 illustrates a fabric or textiles covered embodiment.

Top portion 40 and bottom portion 50 may be integral or may be affixed to one another to form a pouch shaped air cavity 90. As shown in FIG. 1B, both top portion 40 and bottom portion 50 can be recessed in an outward direction. In an alternative embodiment, only one portion can be recessed, while the other portion is a flat member (as shown in FIG. 5). The recessed shape allows air to be retained and flow through cavity 90 during use and also aids in the elastic "rebound" of the top portion 40 after compression. The top and bottom portions may alternatively be sealingly attached to side walls (not shown) which may be elastically deformable and aid in the "rebound" referred to above. A bellows or other design may be adapted for such side walls.

Top portion 40 and bottom portion 50 may be molded integrally or separately by any conventional molding technology, such as injection molding. If formed separately, the portions 40, 50 are sealed together along seal 60, leaving one side or section able to be opened and closed, such as by flap 70 in FIG. 2. The portions can be sealed through use of chemical, thermal or adhesive bonding or alternatively made integrally by a fusion method, such as thermal fusion or solvent welding.

Air holes 20, as shown in FIG. 1A, may be formed in both the top portion 40 and the bottom portion 50 to release scent when mat 10 is stepped on. Air holes 20 can range in size and number, depending of the amount of scent a user prefers to be released from mat 10 during each use. In an area such as a car, a mat containing more air holes may be preferable. Air holes 20 may be formed by molding or by using a punch press or other suitable method. In alternative embodiments, air holes 20 may be in the form of slits or a screen or open mesh area formed on the top portion 40.

Flap 70, as shown in FIG. 2, is formed integrally with top portion 40. However, top portion 40 and bottom portion 50 may be closed in a variety of ways, such as by using velcro, a zipper, snaps or other suitable fastener or closure device. Once flap 70 or other fastener is closed, an air cavity 90 is formed, with entry and exit of air solely through air holes 20. Flap 70 allows for entry and removal of scented inserts 80. As an alternative, mat 10 can be produced as a one time disposable unit that is completely sealed without flap 70. For use in such applications as garbage can liners and litter box underlayment, a disposable unit may be preferred. For such disposable light-duty applications, the mat is preferably made of a low density plastic or plastic film, and may have an adhesive backing for temporary attachment to a surface.

Figure 3A:
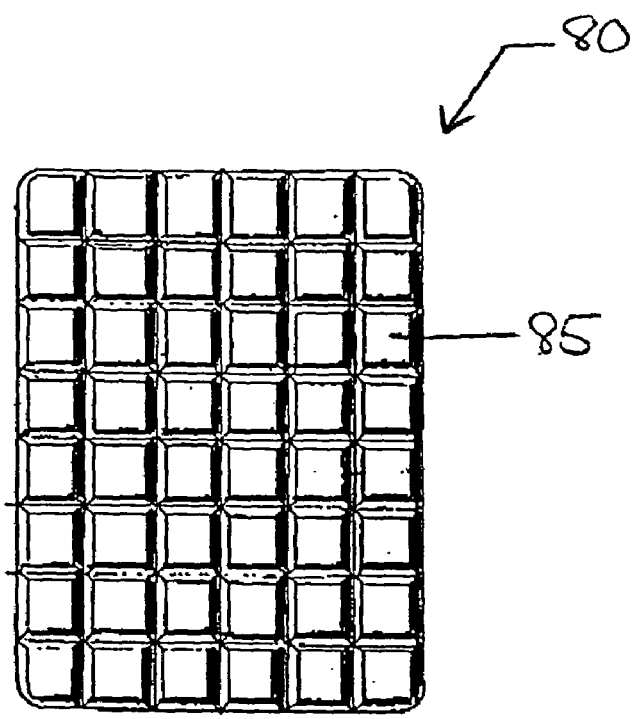
FIG. 3A illustrates one example of a scented insert.
Figure 3B:
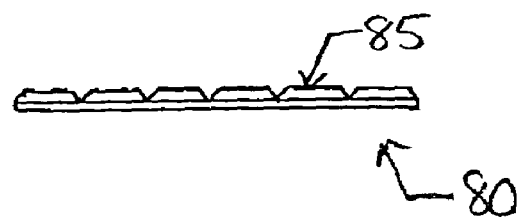
FIG. 3B is a side view thereof.

Turning to FIGS. 3A and 3B, the scented insert 80 is shown having a honeycomb pattern 85. However, insert 80 can have any pattern, shape or size such as a disk, block or wafer. Insert 80 can be made of low density plastic, cotton, sponge, foam, an absorbent porous sheet material, solid material or gel capable of holding and retaining scent, such as a scented oil used in common household deodorizers. A user can replace insert 80, once the oil or scented material dries up, evaporates or otherwise begins to lose its scent. Insert 80 can be infused with a variety of scents, either by a user or during the manufacturing process.

Protrusions 30, shown in FIG. 1B may be made of the same material of mat 10, or any other suitable material. They may be formed integrally with mat 10 or attached thereto using an adhesion method. Protrusions 30 help a user's foot to grip top portion 40 during use. Protrusions 30 on bottom portion 50 can help mat 10 grip and maintain position on the floor or other surface where mat 10 is placed. Alternatively, mat 10 can be manufactured without any protrusions. As shown in FIG. 1B, protrusions 30 are rounded nodules.

Figure 4A:
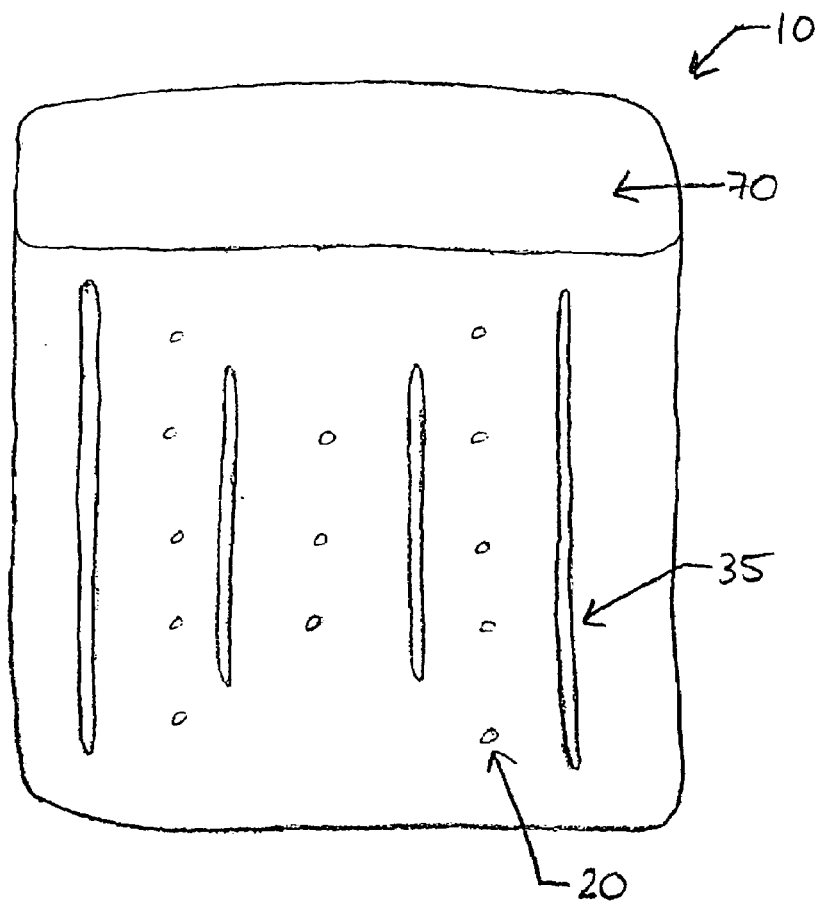
FIGS. 4A and 4B illustrate an additional embodiment in plan and side views, respectively, and further illustrate a rib structure useable with the embodiments.
Figure 4B:
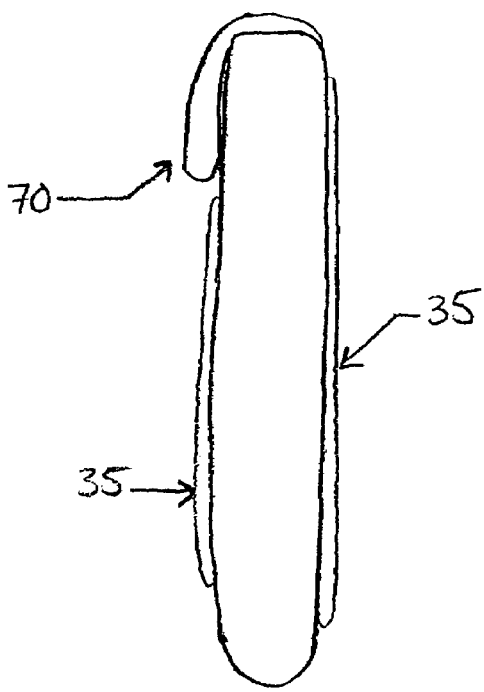

However, they can be of varying size and shape, such as the long ribs 35 of FIGS. 4A and 4B. The ribs 35 can also be in any pattern, such as wavy, diagonal, criss-cross, zigzag or the like.

As shown in FIG. 5, mat 10 contains a covering 100 over top portion 40. Covering 100 can be implemented for either aesthetic or practical uses. In FIG. 5, covering 100 is a carpet overlay for use of mat 10 in a bathroom, entryway, hallway, as an area rug or the like. However, covering 100 can be a material more useful in industrial type settings, such as an outdoor carpeting. Covering 100 helps to conceal mat 10, while still allowing scent from insert 80 to be dispersed through air holes 20. Covering 100 may alternatively be in the form of an arbitrary design, including a breathable fabric into which the mat may be placed.

Figure 6A:
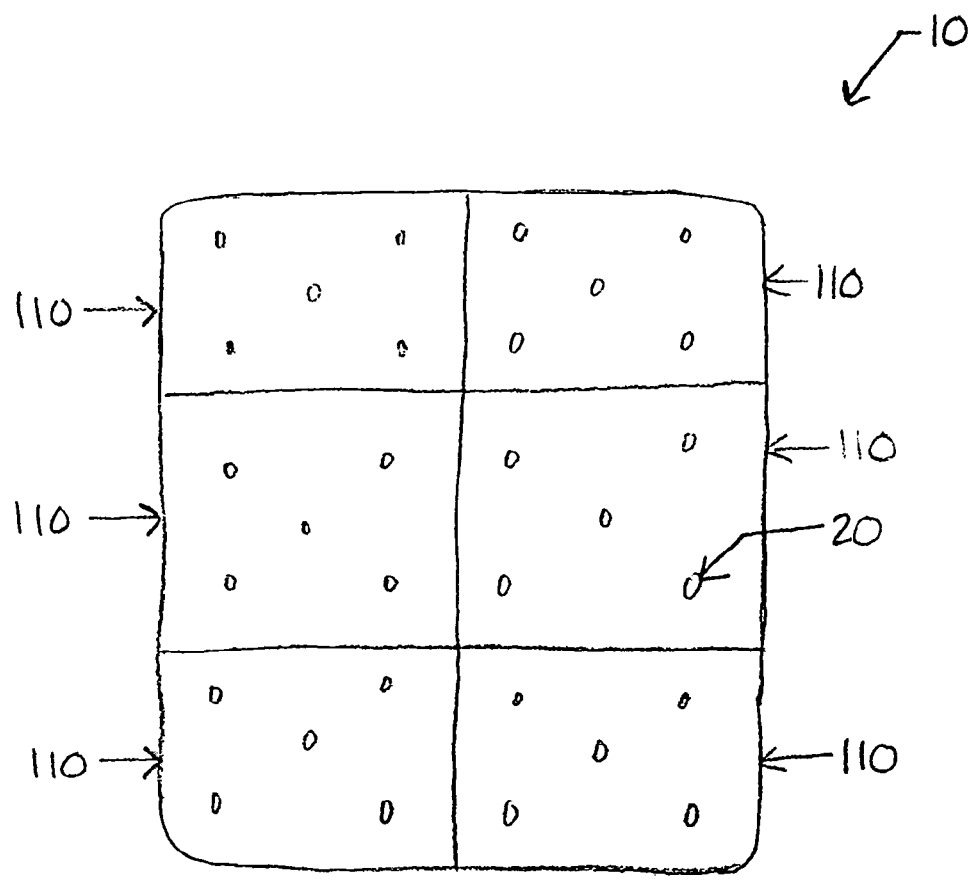
FIGS. 6A and 6B illustrate multi-compartment embodiments.
Figure 6B:
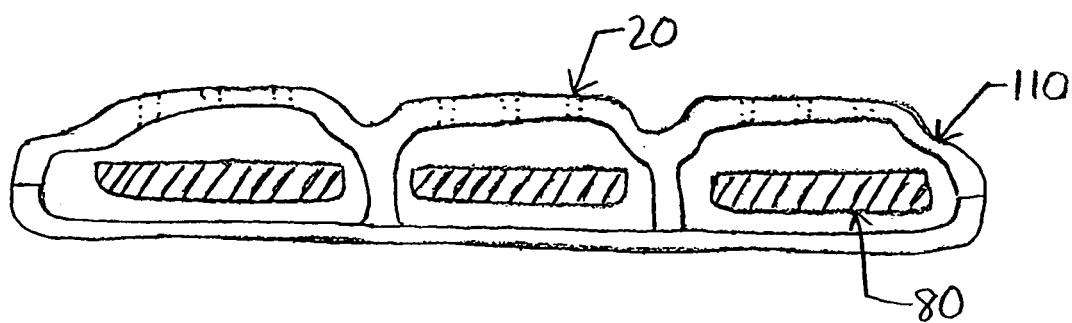

In another illustrative non-limiting embodiment of the present invention, FIGS. 6A and 6B show mat 10 having multiple housings 110 for enclosing scented inserts 80. Each housing 110 is sealed separately from adjoining housings. Housings 110 may contain flap 70 as shown in FIG. 2, or other closing means to prevent inserts 80 from coming loose. Each housing 110 has air holes 20 for dispersion of scent. This non-limiting embodiment can be used for large area rugs or rooms where there is pedestrian traffic covering a large area, such as a restaurant.

Figure 7A:
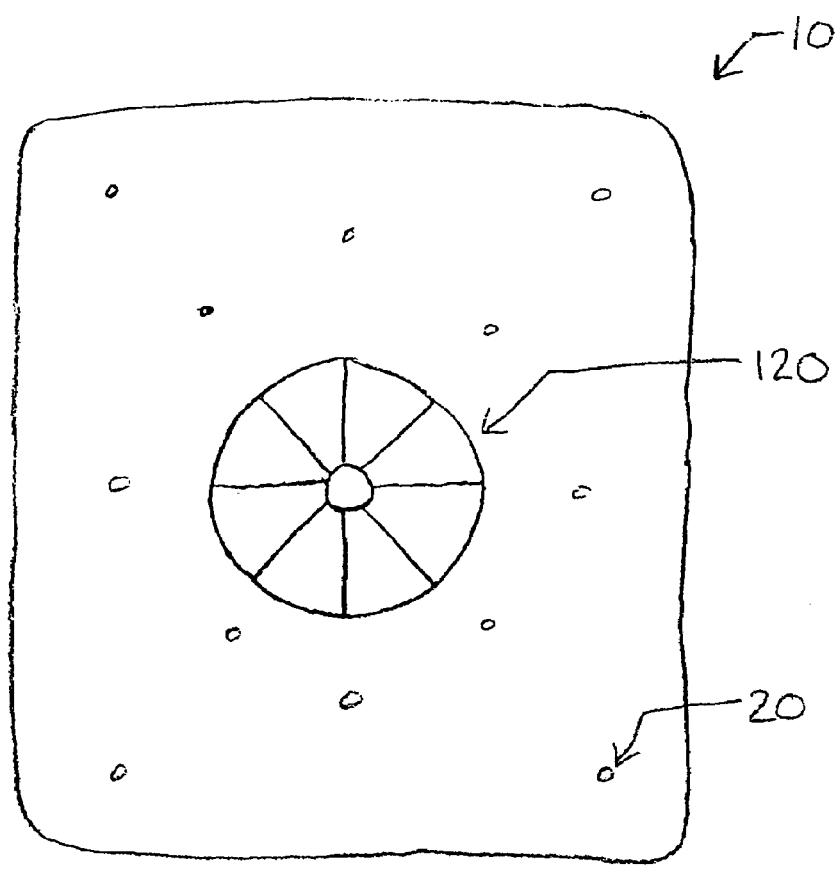
FIG. 7A illustrates an embodiment incorporating a pump unit.
Figure 7B:
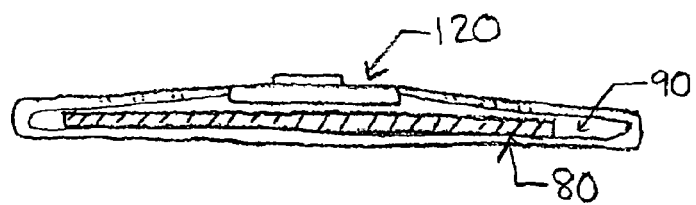
FIG. 7B is a sectional side view of the embodiment of FIG. 7.

As shown in FIGS. 7A and 7B, mat 10 has a pump 120. When a user steps on and compresses pump 120, suction is created which circulates air through air cavity 90 and out through air holes 20. Pump 120 may be attached to or formed integrally with the top portion 40 of mat 10. Pump 120 may be made of plastic or other suitable material. Various types of common pumps, such as a push pump may be implemented.

An interchangeable cartridge insert (not shown) can also be used to house the scented insert 80. The cartridge can be placed in seam 60 along one edge of mat 70. Alternatively, the cartridge insert can have a snapping mechanism to snap in place or a slide and lock mechanism to lock into the side of mat 10. Various types of coverings 100, as described above, can be used to hide the inserted cartridge. The interchangeable cartridge insert allows a user to easily change the scented insert 80 for different scents or for using multiple scents simultaneously. Scented insert 80 can be in the form of a liquid, oil, solid or gel.

The previous descriptions of the preferred embodiments is provided to enable a person skilled in the art to make and use the present invention. Moreover, various modifications to those embodiments will be readily apparent to those skilled in the art. Various modifications may include, use of the scent dispersion apparatus in a dog or cat bed, pillows, car seats, cushions or use as a shoe sole insert, or in a clothing or hair brush. It will be appreciated that the above descriptions are intended only to serve as examples, and that many other embodiments are possible within the spirit and the scope of the present invention. It will also be appreciated that although the invention is described in terms of dispersing a scent, an essentially odorless deodorant or odor-absorbent material is within the invention and within the definition of "scented" as used herein.

What is claimed is:

1. A floor mat, comprising;
a top portion including a plurality of air ventilation apertures;
a bottom portion connected directly or indirectly to said top portion and at least partially sealing an interior space therebetween;
a scent-containing member within said interior space; and
a flap, being integrally formed with said top portion and removably connected to said bottom portion, wherein when said flap is closed, said interior space is completely sealed, with entry and exit of air solely through said air ventilation apertures, and wherein when said flap is opened, access to said interior space is permitted for replacement of said scent-containing member with a new scent-containing member;
wherein, upon application of pressure to said top portion, said floor mat releases scented air to a surrounding area; and upon release of said pressure, said floor mat draws in additional air to be scented.

2. A floor mat, comprising;
a top portion made of a flexible material and including a plurality of air ventilation apertures;
a bottom portion connected directly or indirectly to said top portion and at least partially sealing an interior space therebetween;
a scent-containing member within said interior space; and
a flap, being integrally formed with said top portion and removably connected to said bottom portion, wherein when said flap is closed, said interior space is completely sealed, with entry and exit of air solely through said air ventilation apertures, and wherein when said flap is opened, access to said interior space is permitted for replacement of said scent-containing member with a new scent-containing member;
wherein, upon application of pressure to said top portion, said floor mat releases scented air to a surrounding area through said ventilation apertures; and upon release of said pressure, said floor mat draws in additional air to be scented through said ventilation apertures.

3. A scent dispersing mat structure, comprising;
a top portion including a plurality of air ventilation apertures;
a bottom portion connected directly or indirectly to said top portion and at least partially sealing at least one interior space therebetween;
a scent-containing member within said interior space(s);
a flap, being integrally formed with said top portion and removably connected to said bottom portion, wherein when said flap is closed, said interior space is completely sealed, with entry and exit of air solely through said air ventilation apertures, and wherein when said flap is opened, access to said interior space is permitted for replacement of said scent-containing member with a new scent-containing member;
wherein, upon application of pressure to said top portion, said mat releases scented air to a surrounding area; and upon release of said pressure, said mat draws in additional air to be scented, and a layer of carpeting covering at least said top portion except for said ventilation apertures.

4. A mat as claimed in claim 1, wherein said scented member comprises foam member.

5. A mat as claimed in claim 1, wherein at least one of said top and bottom portions is elastically deformable, so as to draw in said additional air upon release of pressure through a rebound action.

6. A mat as claimed in claim 1, wherein a push pump is integrally formed within said top portion.

7. A mat as claimed in claim 1, wherein each of said top and bottom portions, respectively, further comprise a plurality of protrusions which are integrally formed on the outer surfaces of said top and bottom portions, wherein said protrusions help a user's foot to grip and maintain position on the floor or other surface where said mat is placed.

8. A mat as claimed in claim 1, wherein each of said top and bottom portions, respectively, further comprise a plurality of protrusions in the shape of long ribs which are integrally formed on the outer surfaces of said top and bottom portions, wherein said protrusions help a user's foot to grip and maintain position on the floor or other surface where said mat is placed.

* * * * *